(12) United States Patent
Bru Roig et al.

(10) Patent No.: US 9,950,982 B2
(45) Date of Patent: Apr. 24, 2018

(54) 1-(7,10,10-TRIMETHYL-4-BICYCLO(6.2.0) DECANYL)ETHANONE AS NOVEL AROMA CHEMICAL

(71) Applicant: BASF SE, Ludwigshafen (DE)

(72) Inventors: Miriam Bru Roig, Heidelberg (DE); Stefan Rüdenauer, Weinheim (DE); Ralf Pelzer, Fürstenberg (DE)

(73) Assignee: BASF SE (REITSTÖTTER, KINZEBACH & PARTNER), Ludwigshafen am Rhein (DE)

( * ) Notice: Subject to any disclaimer, the term of this patent is extended or adjusted under 35 U.S.C. 154(b) by 0 days.

(21) Appl. No.: 15/536,452

(22) PCT Filed: Dec. 18, 2015

(86) PCT No.: PCT/EP2015/080388
§ 371 (c)(1),
(2) Date: Jun. 15, 2017

(87) PCT Pub. No.: WO2016/097238
PCT Pub. Date: Jun. 23, 2016

(65) Prior Publication Data
US 2018/0002266 A1 Jan. 4, 2018

(30) Foreign Application Priority Data
Dec. 19, 2014 (EP) .................... 14199389

(51) Int. Cl.
*C07C 49/307* (2006.01)
*C11B 9/00* (2006.01)

(52) U.S. Cl.
CPC .............. *C07C 49/307* (2013.01); *C11B 9/00* (2013.01); *C07C 2602/26* (2017.05)

(58) Field of Classification Search
CPC ................................ C07C 49/307; C11B 9/00
See application file for complete search history.

(56) References Cited

U.S. PATENT DOCUMENTS

| | | | |
|---|---|---|---|
| 7,449,606 B2 | 11/2008 | Teles et al. | |
| 7,838,705 B2 | 11/2010 | Teles et al. | |
| 8,420,866 B2 | 4/2013 | Teles et al. | |
| 8,461,392 B2 | 6/2013 | Teles et al. | |

FOREIGN PATENT DOCUMENTS

| | | |
|---|---|---|
| JP | H11035969 A | 2/1999 |
| JP | H11071312 A | 3/1999 |
| WO | WO-2005030689 A2 | 4/2005 |
| WO | WO-2005030690 A2 | 4/2005 |
| WO | WO-2010023211 A2 | 3/2010 |
| WO | WO-2010076182 A1 | 7/2010 |
| WO | WO-2016097239 A1 | 6/2016 |

OTHER PUBLICATIONS

Collado, I., et al., "Recent advances in the chemistry of caryophyllene", Natural Product Reports, vol. 15, (1998), pp. 187-204.
Hermans, I., et al., "Diazo chemistry controlling the selectivity of olefin ketonisation by nitrous oxide", Physical Chemistry Chemical Physics, vol. 9, No. 31, (2007), pp. 4269-4274.
International Search Report for PCT/EP2015/080388 dated Feb. 17, 2016.
International Search Report for PCT/EP2015/080389 dated May 27, 2016.
Matsubara, Y., et al., "Reinvestigation of oxidation products of β-Caryophyllene with lead tetraacetate", Nippon Nōgeikagaku Kaishi, vol. 59, No. 1, (1985), pp. 19-24 (in German) with Database CAPLUS, Accession No. 1985-560705, XP-002739759 (in English).
Sköld, M., et al., "The fragrance chemical b-caryophyllene—air oxidation and skin sensitization", Food and Chemical Toxicology, vol. 44, (2006), pp. 538-545.
Starkon, K.A., et al., "Liquid Phase Oxidation of Alkenes with Nitrous Oxide to Carbonyl Compounds", Advanced Synthesis Catalysis, vol. 346, No. 2-3, (2004), pp. 268-274.
Uschida, T., et al., "Structures of Two Novel Sesquiterpenoids Formed by the Lead Tetraacetate Oxidation of b-Caryophyllene", Agricultural and Biological Chemistry, vol. 53, No. 11, (1989), pp. 3011-3015.
Written Opinion of the International Searching Authority for PCT/EP2015/080388 dated Feb. 17, 2016.
Written Opinion of the International Searching Authority for PCT/EP2015/080389 dated May 27, 2016.

*Primary Examiner* — Sikarl A Witherspoon
(74) *Attorney, Agent, or Firm* — Drinker Biddle & Reath LLP

(57) ABSTRACT

The present invention relates to 1-(7,10,10-trimethyl-4-bicyclo[6.2.0]decanyl)ethanone, the use of 1-(7,10,10-trimethyl-4-bicyclo[6.2.0]decanyl)ethanone as a fragrance or as flavor, to a method for imparting or modifying a scent or a flavor to a composition by including said compound into such composition, to a fragrance containing composition and/or a fragrance material containing said compound and to a process for preparing 1-(7,10,10-trimethyl-4-bicyclo [6.2.0]decanyl)ethanone.

17 Claims, No Drawings

1-(7,10,10-TRIMETHYL-4-BICYCLO(6.2.0) DECANYL)ETHANONE AS NOVEL AROMA CHEMICAL

CROSS-REFERENCE TO RELATED APPLICATIONS

This application is a national stage application (under 35 U.S.C. § 371) of PCT/EP2015/080388, filed Dec. 18, 2015, which claims benefit of European. Application No. 14199389.9, filed Dec. 19, 2014, both of which are incorporated herein by reference in their entirety.

The present invention relates to 1-(7,10,10-trimethyl-4-bicyclo[6.2.0]decanyl)ethanone, the use of 1-(7,10,10-trimethyl-4-bicyclo[6.2.0]decanyl)ethanone as a fragrance or as flavor, to a method for imparting or modifying a scent or a flavor to a composition by including said compound into such composition, to a fragrance containing composition and/or a fragrance material containing said compound and to a process for preparing 1-(7,10,10-trimethyl-4-bicyclo [6.2.0]decanyl)ethanone.

BACKGROUND OF THE INVENTION

Fragrances are of great interest especially in the field of cosmetics and also laundry and cleaning detergents. Fragrances of natural origin are mostly expensive, often limited in their available amount and, on account of fluctuations in environmental conditions, are also subject to variations in their content, purity etc. To circumvent these undesirable factors, it is therefore of great interest, by way of example, to chemically modify readily available natural substances, e.g. readily available fragrances of natural origin, to create substances, which have organoleptic properties that resembles more expensive natural fragrances or which have novel and interesting organoleptic profiles. Such "semi-synthetic" substances can, by way of example, be used as substitutes for purely natural substances on account of their odor, where substitute and natural substance do not necessarily have to have a chemical-structural similarity.

However, since even small changes in chemical structure may bring about massive changes in the sensory properties such as odor and also taste, the targeted search for substances with certain sensory properties such as a certain odor is extremely difficult. The search for new fragrances and flavorings is therefore in most cases difficult and laborious without knowing whether a substance with the desired odor and/or taste will even actually be found.

There is a constant need for novel aroma chemicals with advantageous sensory properties.

Caryophyllene and its analogs are known fragrance chemicals. Caryophyllene is a natural product, which can readily be isolated from clove oil. Some of its main oxidation products are also described in the state of the art.

Skold et al., Food and Chemical Toxicology, 2006, Vol. 44, pp. 538-545, describe the air oxidation of the fragrance chemical beta-caryophyllene to caryophyllene oxide and its allergenic activity.

Collado et al., Nat. Prod. Reports 1998, Vol. 15, pp. 187-204, for example describe the physical properties and reactivity of beta-caryophyllene in detail, including its oxidation products that are obtained from various oxidation reactions.

Matsubara et al., Nippon Nogei Kagaku Kaishi, 1985, Vol. 59, Nr. 1, pp. 19-24, and Uchida et al., Agric. Biol. Chem., 1989, Vol. 53, Issue 11, pp. 3011-3015, describe the oxidation of beta-caryophyllene with lead tetraacetate and the analytical characterization of the obtained oxidation products. Besides 11 other compounds, they identified 1-[(1R,4R,8S)-10,10-dimethyl-7-methylene-4-bicyclo [6.2.0]decanyl]ethanone and 1-[(1R,4S,8S)-10,10-dimethyl-7-methylene-4-bicyclo[6.2.0]decanyl]ethanone in the oxidation product mixture. Specifically, the oxidation reaction is performed by reacting beta-caryophyllene with lead(IV) acetate in stoichiometric quantities, upon which 1-[(1R,4R, 8S)-10,10-dimethyl-7-methylene-4-bicyclo[6.2.0]decanyl] ethanone and 1-[(1R,4S,8S)-10,10-dimethyl-7-methylene-4-bicyclo[6.2.0]decanyl]ethanone were obtained in a selectivity of 10.2% and 9.9%, respectively. Furthermore, they propose the potential use of these oxidation products in perfumes, due to their mildly woody odor.

SUMMARY OF THE INVENTION

It was an object of the present invention to find substances, which can be used as novel fragrances or flavors and which can be synthesized in large-scale from readily obtainable starting materials. In particular, odor-intensive substances having a pleasant odor are sought. The novel fragrances or flavors should be free from toxicological concerns.

It was surprisingly found, that 1-(7,10,10-trimethyl-4-bicyclo[6.2.0]decanyl)ethanone, in particular 1-[(1R,4R/S, 7R/S,8S)-7,10,10-trimethyl-4-bicyclo[6.2.0]decanyl]ethanone, exhibits pleasant organo-leptical properties and can advantageously be used as a fragrance or as flavor. Especially the isomer 1-[(1R,4S,7R/S,8S)-7,10,10-trimethyl-4-bicyclo[6.2.0]decanyl]ethanone was found to be particularly suitable as a fragrance or as flavor. Furthermore, it was surprisingly found that 1-[(1R,4R/S,7R/S,8S)-7,10,10-trimethyl-4-bicyclo[6.2.0]decanyl]ethanone can be readily obtained by catalytic hydrogenation of 1-[(1R,4R/S,8S)-10, 10-dimethyl-7-methylene-4-bicyclo[6.2.0]decanyl]-ethanone. 1-[(1R,4R/S,8S)-10,10-dimethyl-7-methylene-4-bicyclo[6.2.0]decanyl]-ethanone itself is available from the oxidation of (1R,4E,9S)-4,11,11-trimethyl-8-methylene-bicyclo[7.2.0]undec-4-ene with $N_2O$ in high yields and selectivities.

The present invention relates to 1-(7,10,10-trimethyl-4-bicyclo[6.2.0]decanyl)ethanone and its stereoisomers, in particular to 1-[(1R,4R/S,7R/S,8S)-7,10,10-trimethyl-4-bicyclo[6.2.0]decanyl]ethanone and the stereoisomer mixtures of 1-[(1R,4R/S,7R/S,8S)-7,10,10-trimethyl-4-bicyclo[6.2.0] decanyl]ethanone predominantly containing either the (4R, 7R)- and (4R,7S)-isomers or the (4S,7R)- and (4S,7S)-isomers.

The present invention further relates to stereoisomer mixtures of 1-[(1R,4R/S,7R/S,8S)-7,10,10-trimethyl-4-bicyclo[6.2.0]decanyl]ethanone predominantly containing one of the following isomers, the (4R,7R)-isomer, the (4R,7S)-isomer, the (4S,7R)-isomer or the (4S,7S)-isomer.

The present invention further relates to the use of 1-(7, 10,10-trimethyl-4-bicyclo[6.2.0]decanyl)ethanone, in particular 1-[(1R,4R/S,7R/S,8S)-7,10,10-trimethyl-4-bicyclo [6.2.0]decanyl]ethanone, and to the use of stereoisomer mixtures of 1-[(1R,4R/S,7R/S,8S)-7,10,10-trimethyl-4-bicyclo[6.2.0]decanyl]ethanone predominantly containing either the (4R,7R)- and (4R,7S)-isomers or the (4S,7R)- and (4S,7S) isomers, as a fragrance or as a flavor.

The invention further relates to the use of 1-(7,10,10-trimethyl-4-bicyclo[6.2.0]decanyl)ethanone, in particular 1-[(1R,4R/S,7R/S,8S)-7,10,10-trimethyl-4-bicyclo[6.2.0] decanyl]ethanone, and to the use of stereoisomer mixtures of 1-[(1R,4R/S,7R/S,8S)-7,10,10-trimethyl-4-bicyclo[6.2.0] decanyl]ethanone predominantly containing either the (4R, 7R)- and (4R,7S)-isomers or the (4S,7R)- and (4S,7S)-isomers, as a fragrance or as a flavor, where said compounds or mixture are included into compositions, which is selected from laundry detergents, fabric detergents, cosmetic preparations, fragranced hygiene articles, foods, food supplements, fragrance dispensers, perfumes, pharmaceutical preparations and crop protection compositions.

The invention further relates to a method of imparting or modifying a scent or a flavor to a composition, which method comprises including or incorporating 1-(7,10,10-trimethyl-4-bicyclo[6.2.0]decanyl)ethanone, in particular 1-[(1R,4R/S,7R/S,8S)-7,10,10-trimethyl-4-bicyclo[6.2.0]decanyl]ethanone, or a stereoisomer mixture of 1-[(1R,4R/S,7R/S,8S)-7,10,10-trimethyl-4-bicyclo[6.2.0]decanyl]ethanone predominantly containing either the (4R,7R)- and (4R,7S)-isomers or the (4S,7R)- and (4S,7S)-isomers into a composition in such an amount that imparts or modifies the scent or flavor of the composition.

The invention further relates to a fragrance containing composition and/or a fragrance material, which contains 1-(7,10,10-trimethyl-4-bicyclo[6.2.0]decanyl) ethanone, in particular 1-[(1R,4R/S,7R/S,8S)-7,10,10-trimethyl-4-bicyclo[6.2.0]decanyl]ethanone, or a stereoisomer mixture of 1-[(1R,4R/S,7R/S,8S)-7,10,10-trimethyl-4-bicyclo[6.2.0]decanyl]ethanone predominantly containing either the (4R,7R)- and (4R,7S)-isomers or the (4S,7R)- and (4S,7S)-isomers and a carrier material.

The invention further relates to a process for producing 1-(7,10,10-trimethyl-4-bicyclo[6.2.0]decanyl)ethanone, which comprises providing 1-(10, 10-dimethyl-7-methylene-4-bicyclo[6.2.0]decanyl)ethanone and hydrogenating the composition with hydrogen in the presence of a hydrogenation catalyst.

1-(7,10,10-trimethyl-4-bicyclo[6.2.0]decanyl)ethanone, in particular 1-[(1R,4R/S,7R/S,8S)-7,10,10-trimethyl-4-bicyclo[6.2.0]decanyl]ethanone, and the stereoisomer mixtures of 1-[(1R,4R/S,7R/S,8S)-7,10,10-trimethyl-4-bicyclo[6.2.0]decanyl]ethanone predominantly containing either the (4R,7R)- and (4R,7S)-isomers or the (4S,7R)- and (4S,7S)isomers exhibit the following advantages:

1-(7,10,10-trimethyl-4-bicyclo[6.2.0]decanyl)ethanone, in particular 1-[(1R,4R/S,7R/S,8S)-7,10,10-trimethyl-4-bicyclo[6.2.0]decanyl]ethanone, possesses advantageous sensory properties, in particular a pleasant odor. Therefore, it can be favorably used as a fragrance or as a flavor or as ingredient of a fragrance containing composition and/or a fragrance material.

By virtue of its physical properties, 1-(7,10,10-trimethyl-4-bicyclo[6.2.0]decanyl)ethanone, in particular 1-[(1R,4R/S,7R/S,8S)-7,10,10-trimethyl-4-bicyclo[6.2.0]decanyl]ethanone, has particularly good, virtually universal solvent properties for other fragrances and other customary ingredients in fragrance-comprising preparations such as, in particular, perfumes.

1-(7,10,10-trimethyl-4-bicyclo[6.2.0]decanyl)ethanone can be synthetically produced by using the cheap and readily obtainable starting material 4,11,11-trimethyl-8-methylene-bicyclo[7.2.0]undec-4-ene, which is also termed beta-caryophyllene.

The processes for producing 1-(7,10,10-trimethyl-4-bicyclo[6.2.0]decanyl)ethanone is simple and efficient. 1-(7,10,10-trimethyl-4-bicyclo[6.2.0]decanyl)ethanone can therefore be provided without difficulty on a large industrial scale.

1-(7,10,10-trimethyl-4-bicyclo[6.2.0]decanyl)ethanone, in particular 1-[(1R,4R/S,7R/S,8S)-7,10,10-trimethyl-4-bicyclo[6.2.0]decanyl]ethanone, is likely to have low toxicity as it belongs to a group of oxidation products of (1R,4E,9S)-4,11,11-trimethyl-8-methylene-bicyclo [7.2.0]undec-4-ene, which are in general free from toxicological concerns.

DETAILED DESCRIPTION 1-(7,10,10-trimethyl-4-bicyclo[6.2.0]decanyl)ethanone is a compound of the following formula (I)

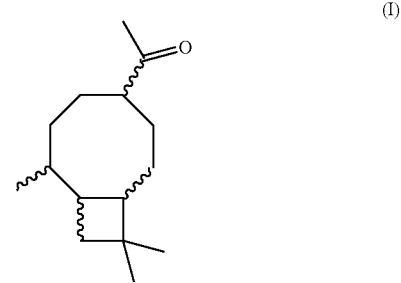 [SMILES: CC(=O)C1CCC(C)C2CC(C)(C)C2CC1]

(I)

It is apparent from formula (I) that carbon atom of the 1-, 4-, 7- and 8-position, may have (R)- or (S)-configuration. Hence, 1-(7,10,10-trimethyl-4-bicyclo[6.2.0]decanyl)ethanone can be present in the form of a total of 16 stereoisomers.

It is apparent that the 8-membered ring may be fused trans or cis with respect to the 4-membered ring, i.e. that the bridgehead hydrogen atoms may be trans or cis. Preference is given to stereoisomers of the formula (I), where the bridgehead hydrogens are located trans with respect to the bond shared by the 4-membered ring and the 8-membered ring.

A preferred embodiment of the present invention relates to 1-(7,10,10-trimethyl-4-bicyclo[6.2.0]decanyl)ethanone in the form of 1-[(1R,4R/S,7R/S,8S)-7,10,10-trimethyl-4-bicyclo[6.2.0]decanyl]ethanone, where the carbon atom a the 1-position has (R)-configuration and the carbon atom at the 8-position has (S)-configuration.

1-[(1R,4R/S,7R/S,8S)-7,10,10-trimethyl-4-bicyclo[6.2.0] decanyl]ethanone is a compound of the following formula (I.a):

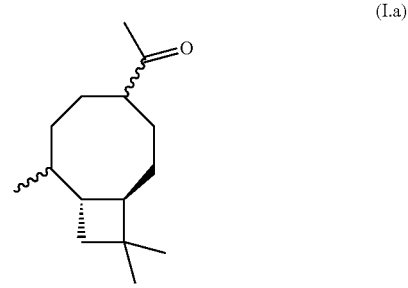

(I.a)

It is apparent from formula (I.a) that carbon atom of the 4-position, which carries the acetyl group, and the carbon atom at the 7-position, which carries the methyl group, may have (R)- or (S)-configuration. Hence, 1-[(1R,4R/S,7R/S, 8S)-7,10,10-trimethyl-4-bicyclo[6.2.0]decanyl]ethanone can be present in the form of the (1R,4R,7R,8S)-isomer 1-[(1R,4R,7R,8S)-7,10,10-trimethyl-4-bicyclo[6.2.0]decanyl]ethanone, hereinafter also termed (4R,7R)-isomer, the (1R,4R,7S,8S)-isomer 1-[(1R,4R,7S,8S)-7,10,10-trimethyl-4-bicyclo[6.2.0]decanyl]ethanone, hereinafter also termed (4R,7S)-isomer, the (1R,4S,7R,8S)-isomer 1-[(1R,4S,7R,8S)-7,10,10-trimethyl-4-bicyclo[6.2.0]decanyl]ethanone, hereinafter also termed (4S,7R)-isomer, or of the (1R,4S,7S,8S)-isomer 1-[(1R,4S,7S,8S)-7,10,10-trimethyl-4-bicyclo[6.2.0]decanyl]ethanone, hereinafter also termed (4S,7S)-isomer, respectively, or in the form of mixtures of the (1R,4R,7R,8S)-, (1R,4R,7S,8S)-, (1R,4S,7R,8S)- and the (1R,4S,7S,8S)-isomer, hereinafter termed (4R/S,7R/S)-isomer mixtures.

The invention relates both to the (1R,4R,7R,8S)-, (1R,4R,7S,8S)-, (1R,4S,7R,8S)- or the (1R,4S,7S,8S)-stereoisomer of 1-[(1R,4R/S,7R/S,8S)-7,10,10-trimethyl-4-bicyclo[6.2.0]decanyl]ethanone and to the mixtures of these stereoisomers. The term "1-[(1R,4R/S,7R/S,8S)-7,10,10-trimethyl-4-bicyclo[6.2.0]decanyl]ethanone" encompasses both the pure (1R,4R,7R,8S)-isomer, the pure (1R,4R,7S,8S)-isomer, the pure (1R,4S,7R,8S)-isomer and the pure (1R,4S,7S,8S)-isomer, as well as mixtures, where these stereoisomers are present in equal amounts or wherein one or two of these stereoisomers are present in excess.

Frequently, 1-[(1R,4R/S,7R/S,8S)-7,10,10-trimethyl-4-bicyclo[6.2.0]decanyl]ethanone is present as (4R/S,7R/S)-isomer mixtures.

In a particular embodiment of the invention 1-[(1R,4R/S,7R/S,8S)-7,10,10-trimethyl-4-bicyclo[6.2.0]decanyl]ethanone is present in the form of a mixture of (4R/S,7R/S)-stereoisomers thereof, which predominantly contains either the (4R,7R)- and (4R,7S)-isomers, hereinafter termed (4R,7R/S)-isomers, or the (4S,7R)- and (4S,7S)-isomers, hereinafter termed (4S,7R/S)-isomers. More specifically, in these mixtures, either the (4R,7R/S)- or the (4S,7R/S)-isomers of 1-[(1R,4R/S,7R/S,8S)-7,10,10-trimethyl-4-bicyclo[6.2.0]decanyl]ethanone are present in an amount of at least 55% by weight, in particular of at least 65% by weight, based on the total amount of the four stereoisomers of 1-[(1R,4R/S,7R/S,8S)-7,10,10-trimethyl-4-bicyclo[6.2.0]decanyl]ethanone.

In a further particular embodiment of the invention 1-[(1R,4R/S,7R/S,8S)-7,10,10-trimethyl-4-bicyclo[6.2.0]decanyl]ethanone is present in the form of a mixture of (4R/S,7R/S)-stereoisomers thereof, which predominantly contains the (4R,7R)-isomer, or the (4R,7S)-isomer, or the (4S,7R)-isomer or the (4S,7S)-isomer. More specifically, in these mixtures, the (4R,7R)-isomer, or the (4R,7S)-isomer, or the (4S,7R)-isomer or the (4S,7S)-isomer of 1-[(1R,4R/S,7R/S,8S)-7,10,10-trimethyl-4-bicyclo[6.2.0]decanyl]ethanone is present in an amount of at least 30% by weight, in particular of at least 40% by weight, based on the total amount of the four stereoisomers of 1-[(1R,4R/S,7R/S,8S)-7,10,10-trimethyl-4-bicyclo[6.2.0]decanyl]ethanone.

In a special embodiment, the 1-(7,10,10-trimethyl-4-bicyclo[6.2.0]decanyl)ethanone, in particular 1-[(1R,4R/S,7R/S,8S)-7,10,10-trimethyl-4-bicyclo[6.2.0]decanyl]ethanone, or the (4R/S,7R/S)-stereoisomer mixtures of 1-[(1R,4R/S,7R/S,8S)-7,10,10-trimethyl-4-bicyclo[6.2.0]decanyl]ethanone, as defined above, have a purity of at least 80%, in particular at least 90%.

The preferred embodiments mentioned above may be combined arbitrarily with one another.

Accordingly, a particular embodiment of the invention relates to mixtures of the (4R/S,7R/S)-stereoisomers of 1-[(1R,4R/S,7R/S,8S)-7,10,10-trimethyl-4-bicyclo[6.2.0]decanyl]ethanone, which contain the (4R,7R/S)—isomers in an amount of at least 55% by weight, based on the total amount of the (4R/S,7R/S)-stereoisomers of 1-[(1R,4R/S,7R/S,8S)-7,10,10-trimethyl-4-bicyclo[6.2.0]decanyl]ethanone, where said mixture has a purity of at least 80%.

Likewise, a particular embodiment of the invention relates to mixtures of the (4R/S,7R/S)-stereoisomers of 1-[(1R,4R/S,7R/S,8S)-7,10,10-trimethyl-4-bicyclo[6.2.0]decanyl]ethanone, which contain the (4S,7R/S)-isomers in an amount of at least 55% by weight, based on the total amount of the 4R/S,7R/S)-stereoisomers of 1-[(1R,4R/S,7R/S,8S)-7,10,10-trimethyl-4-bicyclo[6.2.0]decanyl]ethanone, where said mixture has a purity of at least 80%.

Likewise, a particular embodiment of the invention relates to mixtures of the (4R/S,7R/S)-stereoisomers of 1-[(1R,4R/S,7R/S,8S)-7,10,10-trimethyl-4-bicyclo[6.2.0]decanyl]ethanone, which contain the (4R,7R)-isomer, the (4R,7R)-isomer, the (4S,7R)-isomer or the (4S,7S)-isomer in an amount of at least 30% by weight, based on the total amount of the four stereoisomers of 1-[(1R,4R/S,7R/S,8S)-7,10,10-trimethyl-4-bicyclo[6.2.0]decanyl]ethanone, where said mixture has a purity of at least 80%.

As previously mentioned, it has been found that 1-(7,10,10-trimethyl-4-bicyclo[6.2.0]decanyl)ethanone, in particular 1-[(1R,4R/S,7R/S,8S)-7,10,10-trimethyl-4-bicyclo[6.2.0]decanyl]ethanone, possesses advantageous sensory properties, in particular a pleasant odor. More specifically, 1-(7,10,10-trimethyl-4-bicyclo[6.2.0]decanyl)ethanone, in particular 1-[(1R,4R/S,7R/S,8S)-7,10,10-trimethyl-4-bicyclo[6.2.0]decanyl]ethanone and especially 1-[(1R,4S,7R/S,8S)-7,10,10-trimethyl-4-bicyclo[6.2.0]decanyl]ethanone exhibits an intensive odor of largely woody, ambery, musky, sweet and female character.

Intensive odor impressions are to be understood as meaning those properties of aroma chemicals which permit a precise perception even at very low gas-space concentrations. The intensity can be ascertained via a threshold-value determination. A threshold value is the concentration of a substance in the relevant gas space at which an odor impression can just still be perceived by a representative test panel, although it no longer has to be defined. The substance class known as probably one of the most odor-intensive, i.e. those with very low threshold values, are thiols, whose threshold value is in the ppb/m$^3$ range. It is the aim of the search for new aroma chemicals to find substances with the lowest possible threshold value in order to permit the lowest possible use concentration. The closer one comes to this target, the more one talks of "intensive" odor substances or aroma chemicals.

"Pleasant odors" or "Advantageous sensory properties" are hedonic expressions which describe the niceness and preciseness of an odor impression conveyed by an aroma chemical.

"Niceness" and "preciseness" are terms which are familiar to the person skilled in the art, a perfumer. Niceness generally refers to a spontaneously brought about, positively perceived, pleasant sensory impression. However, "nice" does not have to be synonymous with "sweet". "Nice" can also describe the odor of musk or sandalwood. "Preciseness" generally refers to a spontaneously brought about sensory impression which—for the same test panel—brings about a reproducibly identical reminder of something specific.

For example, a substance can have an odor which is spontaneously reminiscent of that of an "apple": the odor would then be precisely of "apples". If this apple odor were very pleasant because the odor is reminiscent, for example, of a sweet, fully ripe apple, the odor would be termed "nice". However, the odor of a typically tart apple can also be precise. If both reactions arise upon smelling the substance, in the example thus a nice and precise apple odor, then this substance has particularly advantageous sensory properties.

The invention further relates to the use of 1-(7,10,10-trimethyl-4-bicyclo[6.2.0]decanyl)ethanone, in particular 1-[(1R,4R/S,7R/S,8S)-7,10,10-trimethyl-4-bicyclo[6.2.0] decanyl]ethanone, or (4R/S,7R/S)-stereoisomer mixtures of 1-[(1R,4R/S,7R/S,8S)-7,10,10-trimethyl-4-bicyclo[6.2.0] decanyl]ethanone, as defined above, in compositions, which typically comprise at least one aroma compound, i.e. at least one fragrance and/or flavoring. Such compositions include, for example, laundry detergents, fabric detergents, cosmetic preparations, other fragranced hygiene articles, such as diapers, sanitary towels, armpit pads, paper towels, wet wipes, toilet paper, pocket tissues, and the like, foods, food supplements, examples being chewing gums or vitamin products, fragrance dispensers, examples being room air fresheners, perfumes, pharmaceutical preparations, and also crop protection products.

Typically, these compositions are formulated by incorporating 1-(7,10,10-trimethyl-4-bicyclo[6.2.0]decanyl)ethanone, in particular 1-[(1R,4R/S,7R/S,8S)-7,10,10-trimethyl-4-bicyclo[6.2.0]decanyl]ethanone, or the above defined (4R/S,7R/S)-stereoisomer mixtures of 1-[(1R,4R/S,7R/S,8S)-7,10,10-trimethyl-4-bicyclo[6.2.0]decanyl]ethanone, optionally together with one or more other aroma compounds, into an existing preparation, which before comprises no aroma compound or which before comprises one or more other aroma compound different from 1-(7,10,10-trimethyl-4-bicyclo[6.2.0]decanyl)ethanone. Such compositions generally further comprise a carrier, which may be a compound, a compound mixture or other additives, which have no or no noticeable sensory properties. The carrier may as well be a compound or an additive having noticeable sensory properties, or a compound mixture comprising one or more other aroma compounds different from compounds 1-(7,10,10-trimethyl-4-bicyclo[6.2.0]decanyl)ethanone and optionally one or more compounds having no or no noticeable sensory properties.

In the compositions according to the present invention 1-(7,10,10-trimethyl-4-bicyclo[6.2.0]decanyl)ethanone, in particular 1-[(1R,4R/S,7R/S,8S)-7,10,10-trimethyl-4-bicyclo[6.2.0]decanyl]ethanone and its (4R/S,7R/S)-stereoisomers mixtures, as defined above, are usually applied in amounts customary for formulation auxiliaries. More specifically the amount of 1-(7,10,10-trimethyl-4-bicyclo [6.2.0]decanyl)ethanone is in the range of 0.001 to 50% by weight, in particular in the range of 0.01 to 20% by weight, especially in the range of 0.1 to 10% by weight, based on the total weight of the composition.

1-(7,10,10-trimethyl-4-bicyclo[6.2.0]decanyl)ethanone, in particular 1-[(1R,4R/S,7R/S,8S)-7,10,10-trimethyl-4-bicyclo[6.2.0]decanyl]ethanone, preferably find use in laundry detergents and fabric detergents, in cosmetic preparations and in other fragranced hygiene articles. Particular preference is given to the use of 1-(7,10,10-trimethyl-4-bicyclo [6.2.0]decanyl)ethanone, in particular 1-[(1R,4R/S,7R/S, 8S)-7,10,10-trimethyl-4-bicyclo[6.2.0]decanyl]ethanone, in cosmetic preparations such as perfumes.

The invention further relates to a method of imparting or modifying a scent or a flavor to a composition, which method comprises including or incorporating 1-(7,10,10-trimethyl-4-bicyclo[6.2.0]decanyl)ethanone, in particular 1-[(1R,4R/S,7R/S,8S)-7.10.10-trimethyl-4-bicyclo[6.2.0] decanyl]ethanone, into a composition in such an amount that imparts or modifies the scent or flavor of the composition. The total amount of 1-(7,10,10-trimethyl-4-bicyclo[6.2.0] decanyl)ethanone required for modification depends on the nature and on the application purpose of the composition and can, therefore, vary in a wide range. Typically, the total amount of 1-(7,10,10-trimethyl-4-bicyclo[6.2.0]decanyl) ethanone included/incorporated into the composition is in the range of from 0.001 to 50% by weight, in particular in the range of from 0.01 to 20% by weight, based on the total weight of the composition.

The intensively and precisely smelling 1-(7,10,10-trimethyl-4-bicyclo[6.2.0]decanyl)ethanone is preferably used as fragrance. Suitable fields of application are all applications in which a certain odor is desired, whether it is to mask more unpleasant odors or to generate a certain odor or certain odor notes in a targeted manner.

Therefore, the invention further relates to a fragrance containing composition and/or a fragrance material, which contains 1-(7,10,10-trimethyl-4-bicyclo[6.2.0]decanyl)ethanone, in particular 1-[(1R,4R/S,7R/S,8S)-7,10,10-trimethyl-4-bicyclo[6.2.0]decanyl]ethanone, and a carrier material.

The total concentration of 1-(7,10,10-trimethyl-4-bicyclo [6.2.0]decanyl)ethanone in the fragrance containing composition and/or the fragrance material according to the present invention is not particularly limited. It can be varied over a wide range, depending on the purpose of their use. Generally, amounts that are customary for fragrances are used. The total amount of 1-(7,10,10-trimethyl-4-bicyclo[6.2.0]decanyl)ethanone in the fragrance containing composition and/or the fragrance material is typically in the range of from 0.001 to 20% by weight, in particular in the range of from 0.01 to 10% by weight, based on the total weight of the fragrance containing composition and/or the fragrance material.

The carrier material may be a compound, a compound mixture or other additives having the properties as defined above. Suitable carrier materials may comprise liquid or oil-based carrier materials as well as wax-like or solid carrier materials.

Suitable liquid or oil-based carrier materials are for example selected from water, alcohols, such as ethanol, aliphatic diols and polyols having melting temperatures below 20° C., such as ethylene glycol, glycerol, diglycerol, propylene glycol or dipropylene glycol, cyclic siloxanes (silicon fluids), such as hexamethylcyclotrisiloxane or decamethylcyclopentasiloxane, plant-oils, such as fractionated coconut-oil, or esters of fatty alcohols having melting temperatures below 20° C., such as myristyl acetate or myristyl lactate, and alkyl esters of fatty acids having melting temperatures below 20° C., such as isopropyl-myristate.

Suitable wax-like or solid carrier materials are for example selected from fatty alcohols having melting temperatures above 20° C., such as myristyl alcohol, stearyl alcohol or cetyl alcohol, polyols and esters of fatty alcohol having melting temperatures above 20° C., synthetic petroleum derived waxes, such as paraffin waxes, water insoluble porous minerals, such as silica, silicates, for example talc, microporous aluminasilicate minerals (zeolites), clay minerals, for example bentonite, or phosphates for example sodium tripolyphosphate, paper, cardboard, wood, nonwoven of rayon staple fibers or fiber-fleeces.

Suitable carrier materials are for example also selected from water-soluble polymers, such as polyacrylic acid esters or quaternized polyvinyl pyrrolidone or water-alcohol-soluble polymers, such as specific thermoplastic polyesters and polyamides. The polymeric carrier material can be present in different forms, for example in form of a gel, a paste, or water insoluble solid particles, such as microcapsules or friable coatings.

Depending on the purpose of use, the carrier materials may further comprise other additives or auxiliaries, for example surfactants or mixtures of surfactants, viscosifiers, such as polyethylene glycols with a molecular weight of 400 to 20'000 Da, lubricates, binding or agglomerating agents, such as sodium silicate, dispersing agents, detergent builder salts, filler salts, pigments, dyes, optical brighteners, anti-redeposition agents and the like.

Typical applications of the composition and/or the fragrance material according to the present invention are in the field of laundry and cleaning detergents, preparations of fragrances for the human or animal body, for rooms, such as kitchens, wet rooms, automobiles or heavy goods vehicles, for real or artificial plants, for clothing, for shoes and shoe insoles, for items of furniture, for carpets, for air humidifiers and air fresheners, and for cosmetics, such as perfumes.

Part of the invention are also odorant combinations which comprise 1-(7,10,10-trimethyl-4-bicyclo[6.2.0]decanyl)ethanone, in particular 1-[(1R,4R/S,7R/S,8S)-7,10,10-trimethyl-4-bicyclo[6.2.0]decanyl]ethanone or the above defined stereoisomeric mixtures thereof, as component A and at least one further compound known as an odorant or aroma substance, as component B, such as, for example, one or more of the following compounds B1 to B11:

B1: methyl dihydrojasmonate (e.g. hedione),
B2: 4,6,6,7,8,8-hexamethyl-1,3,4,6,7,8-hexahydrocyclopenta[g]benzopyran (e.g. Galaxolide™),
B3: 2-methyl-3-(4-tert-butylphenyl)propanal (Lysmeral™),
B4: 2-methyl-3-(4-isopropylphenyl)propanal (cyclamenaldehyde),
B5: 2,6-dimethyl-7-octen-2-ol (dihydromyrcenol),
B6: 3,7-dimethyl-1,6-octadien-3-ol (linalool),
B7: 3,7-dimethyl-trans-2,6-octadien-1-ol (geraniol),
B8: 2,3,8,8-tetramethyl-1,2,3,4,5,6,7,8-octahydro-2-naphthalenyl methyl ketone (Iso E Super™),
B9: alpha-hexylcinnamaldehyde,
B10: 3,7-dimethyl-6-octen-1-ol (citronellol),
B11: alpha- or beta- or delta-damascone.

Suitable formulations of odor substances are, for example, the formulations disclosed in JP 11-071312 A, paragraphs [0090] to [0092]. The formulations from JP 11-035969 A, paragraphs [0039] to [0043] are also likewise suitable.

The invention further provides a process for preparing 1-(7,10,10-trimethyl-4-bicyclo[6.2.0]decanyl)ethanone, which comprises
 i) providing 1-(10,10-dimethyl-7-methylene-4-bicyclo[6.2.0]decanyl)ethanone,
 ii) hydrogenating 1-(10,10-dimethyl-7-methylene-4-bicyclo[6.2.0]decanyl)ethanone with hydrogen in the presence of a hydrogenation catalyst.

The invention in particular provides a process for preparing 1-[(1R,4R/S,7R/S,8S)-7,10,10-trimethyl-4-bicyclo[6.2.0]decanyl]ethanone, which comprises
 i) providing 1-[(1R,4R/S,8S)-10,10-dimethyl-7-methylene-4-bicyclo[6.2.0]decanyl]ethanone,
 ii) hydrogenating 1-[(1R,4R/S,8S)-10,10-dimethyl-7-methylene-4-bicyclo[6.2.0]decanyl]ethanone with hydrogen in the presence of a hydrogenation catalyst.

Step i)

1-(10,10-Dimethyl-7-methylene-4-bicyclo[6.2.0]decanyl)ethanone provided in step i), and which is used as the starting material of the hydrogenation reaction in step ii), may have (R)- or (S)-configuration at the carbon atoms of the 1-, 4- and 8-position. Hence, 1-(10,10-Dimethyl-7-methylene-4-bicyclo[6.2.0]decanyl)ethanone can be present in the form of a total of 8 stereoisomers.

The 8-membered ring of 1-(10,10-Dimethyl-7-methylene-4-bicyclo[6.2.0]decanyl)ethanone may be fused trans or cis with respect to the 4-membered ring, i.e. the bridgehead hydrogen atoms may be trans or cis. Preference is given to stereoisomers of 1-(10,10-Dimethyl-7-methylene-4-bicyclo[6.2.0]decanyl)ethanone, where the bridgehead hydrogens are located trans with respect to the bond shared by the 4-membered ring and the 8-membered ring.

1-[(1R,4R/S,8S)-10,10-Dimethyl-7-methylene-4-bicyclo[6.2.0]decanyl]ethanone provided in step i), and which is used as the preferred starting material of the hydrogenation reaction in step ii), may have (R)- or (S)-configuration at the carbon atom of the 4-position, which carries the acetyl group. Hence, 1-[(1R,4R/S,8S)-10,10-dimethyl-7-methylene-4-bicyclo[6.2.0]decanyl]ethanone can be present either in the form of the (1R,4R,8S)-isomer 1-[(1R,4R,8S)-10,10-dimethyl-7-methylene-4-bicyclo[6.2.0]decanyl]-ethanone, hereinafter also termed 4R-isomer, or of the (1R,4S,8S)-isomer 1-[(1R,4S,8S)-10,10-dimethyl-7-methylene-4-bicyclo[6.2.0]decanyl]ethanone, hereinafter termed 4S-isomer, respectively, or in the form of mixtures of the (1R,4R,8S)-isomer and the (1R,4S,8S)-isomer, hereinafter termed 4R/4S-isomer mixtures.

The term "1-[(1R,4R/S,8S)-10,10-dimethyl-7-methylene-4-bicyclo[6.2.0]decanyl]ethanone" encompasses both the pure (1R,4R,8S)-isomer and (1R,4S,8S)-isomer, as well as mixtures, where these stereoisomers are present in equal amounts or wherein one of these stereoisomers is present in excess.

Typically, the 1-[(1R,4R/S,8S)-10,10-dimethyl-7-methylene-4-bicyclo[6.2.0]decanyl]ethanone provided in step i) is present as 4R/4S-isomer mixtures. Particularly, the 1-[(1R,4R/S,8S)-10,10-dimethyl-7-methylene-4-bicyclo[6.2.0]decanyl]ethanone provided in step i) is present in the form of a mixture of 4R/4S-stereoisomers thereof, which predominantly contains either the 4R-isomer or the 4S-isomer. More specifically, in these mixtures, either the 4R- or the 4S-isomer of 1-[(1R,4R/S,8S)-10,10-dimethyl-7-methylene-4-bicyclo[6.2.0]decanyl]-ethanone is present in an amount of at least 55% by weight, in particular of at least 65% by weight, based on the total amount of the 4R- and 4S-isomers of 1-[(1R,4R/S,8S)-10,10-dimethyl-7-methylene-4-bicyclo[6.2.0]decanyl]ethanone.

It is preferred that 1-(10,10-dimethyl-7-methylene-4-bicyclo[6.2.0]decanyl)ethanone and its stereoisomers, in particular 1-[(1R,4R/S,8S)-10,10-dimethyl-7-methylene-4-bicyclo[6.2.0]decanyl]ethanone or the 4R/4S-stereoisomer mixtures thereof, as defined above, provided in step i) has a purity of at least 80%, in particular at least 90%.

In a preferred embodiment of the present process, the 1-(10,10-dimethyl-7-methylene-4-bicyclo[6.2.0]decanyl)ethanone provided in step i) is obtained by reacting 4,11,11-trimethyl-8-methylene-bicyclo[7.2.0]undec-4-ene (beta-caryophyllene) with $N_2O$.

In a preferred variant of this embodiment, (1R,4E,9S)-4,11,11-trimethyl-8-methylene-bicyclo[7.2.0]undec-4-ene is reacted with $N_2O$ to obtain 1-[(1R,4R/S,8S)-10,10-dimethyl-7-methylene-4-bicyclo[6.2.0]decanyl]ethanone, which is then used as starting material of the hydrogenation reaction in step ii).

The oxidation of an olefinic C=C-double bond in olefinically unsaturated organic compounds with $N_2O$ is principally known in the art and can be applied by analogy to the reaction of 1-methyl cyclohexene or similar olefins with $N_2O$—see for example Starokon et al., Adv. Synth. Catal. 2004, Vol. 346, pp. 268-274, Hermans et al., Phys. Chem. Chem. Phys., 2007, Vol. 9, pp. 4269-4274, Romanenko et al., Russ. Chem. Bull. Int. Ed. 2007, Vol. 56, pp. 1239-43 (Oxidation von Terpenen mit $N_2O$), WO 2005/030690, WO 2005/030689, WO 2010/023211 and WO 2010/0076182 (technical oxidation of olefins with N₂O).

To this end, beta-caryophyllene in the form of liquid phase is heated in the presence of N₂O. To increase the solubility of N₂O in the liquid phase, the reaction is preferably performed at elevated pressure.

The reaction is in particular performed at a pressure, in particular at a N₂O pressure, in the range of 5 to 325 bar, preferably in the range of 20 to 250 bar, especially in the range from 60 to 200 bar.

The oxidation can be designed to take place either continuously or batchwise, preference being given here to the continuous design of the process. The batchwise oxidation can be conducted in a reaction apparatus conventionally used for this purpose, e.g. a stirred reactor. It is preferable that the oxidation according to the present invention is carried out continuously, e.g. in a tube reactor or in a cascade of at least three back-mixed reactors. The reactors can be operated isothermal or adiabatic.

Typically, the oxidation reaction is performed without adding a catalyst.

The oxidation reaction is usually carried out in the temperature range from 100 to 300° C., preferably from 130 to 290° C., in particular in the range from 150 to 280° C.

The oxidation reaction can be carried out in bulk, i.e. in the absence of any added solvent or in the presence of one or more organic solvents.

If the oxidation reaction is carried out in the presence of an organic solvent, it is preferred that the organic solvent is inert under the reaction conditions. Preferred inert organic solvents are, by way of example, aliphatic or alicyclic hydrocarbons, in particular alkanes and cycloalkanes having 5 to 12 carbon atoms, halogenated aliphatic hydrocarbons, and aromatic and substituted aromatic hydrocarbons and aliphatic or alicyclic ethers. Examples of inert solvents are aliphatic hydrocarbons, such as pentane, hexane, heptane, ligroin, petrol ether, cyclohexane, halogenated hydrocarbons, such as dichloromethane, trichloromethane, tetrachloromethane or dichloroethane, aromatics, such as benzene, toluene, xylenes, chlorobenzene, dichlorobenzenes, ethers such as methyl-tert.-butylether, dibutyl ether, tetrahydrofurate, 1,4-dioxane, 1,2-dimethoxyethane and mixtures thereof.

If the oxidation reaction is carried out in the presence of an inert organic solvent, the amount of the solvent in the reaction mixture is preferably less than 90% by weight, preferably less than 80% by weight, based on the amount of beta-caryophyllene.

In particular, the oxidation is carried out in the absence of an inert organic solvent.

The oxidation reaction can take place in the absence of or in the presence of an inert gas. The expression inert gas generally means a gas which under the prevailing reaction conditions does not enter into any reactions with the starting materials, reagents, or solvents participating in the reaction, or with the resultant products. Examples of inert gases are N₂, CO₂ and noble gases like He, Ne, Ar, Kr and Xe. It is preferable that the dimerization reaction takes place without addition of any inert gas.

In particular, the molar ratio of N₂O to beta-caryophyllene used in the oxidation reaction is in the range of 1:50 to 10:1, preferably in the range of 1:20 to 5:1, in particular in the range of 1:10 to 1:1

Preferable, the reaction conditions and in particular the amount of N₂O, the reaction pressure, reaction temperature and the reaction time is chosen such that the conversion rate of beta-caryophyllene is in the range of 10 to 98%, in particular in the range of 30 to 90% or in the range of 50 to 85%.

The oxidation reaction of the present process provides 1-(10,10-dimethyl-7-methylene-4-bicyclo[6.2.0]decanyl) ethanone, in particular 1-[(1R,4R/S,8S)-10,10-dimethyl-7-methylene-4-bicyclo[6.2.0]decanyl]ethanone, in good yield and selectivity. Surprisingly, N₂O preferentially reacts with the trisubstituted endocyclic double bond of beta-caryophyllene. In view of the low conversion rates for the oxidation of 1-methyl cyclohexane with N₂O described in the prior art, a skilled person would have expected, that N₂O would also react with the exocyclic double bond at comparable reaction rates. However, the main observed reaction stems from the [2+3]-cycloaddition of N₂O to the trisubstituted endocyclic double bond followed by the elimination of N₂ and a rearrangement of the carbon skeleton.

Generally, the crude product mixture obtained by the above described oxidation reaction may comprise further reaction products. In particular, if (1R,4E,9S)-4,11,11-trimethyl-8-methylene-bicyclo[7.2.0]undec-4-ene is used as the starting material of the oxidation reaction, the crude product mixture may contain, in addition to the main product of formula I.b, further products of the general formulae (II) to (V).

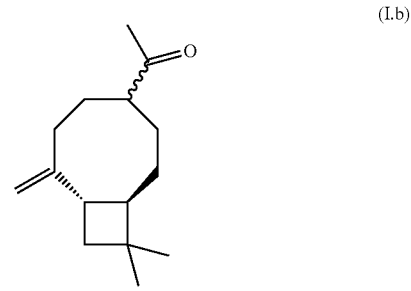

(I.b)

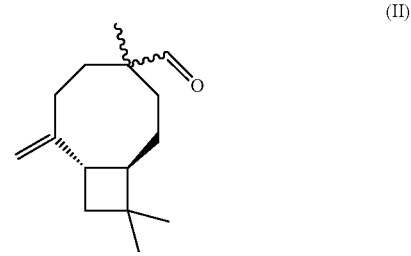

(II)

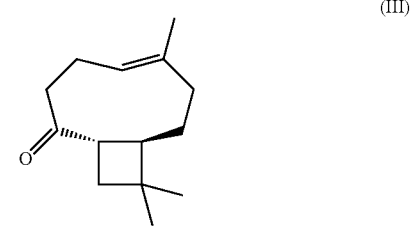

(III)

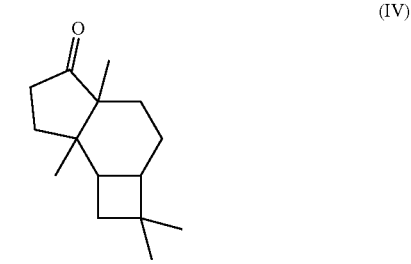

(IV)

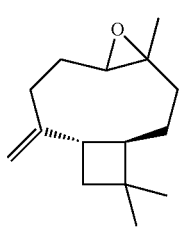

Surprisingly, the ketone of formula (VI),

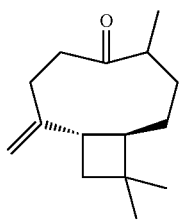

which, by analogy to the known oxidation of 1-methyl cyclohexene using $N_2O$, might be expected to be the major oxidation product of beta-caryophyllene, is typically not found among the reaction products in detectable amounts. The detection limit of the gas-chromatographic analysis system used is estimated to be about 10 wt.-ppm.

As mentioned above, compound (I.b) has been described by Matsubara et al., Nippon Nogei Kagaku Kaishi, 1985, Vol. 59, Nr. 1, pp. 19-24, and Uchida et al., Agric, Biol. Chem., 1989, Vol. 53, Issue 11, pp. 3011-3015. Compound (II) has been described previously as one of the products formed by hydrolysis of caryophyllene oxide (Yang et al., J. Nat. Prod. 1994, Vol. 57, pp. 514). The nor-ketone (III) is also a known product (compound 9 of Collado et al., Nat. Prod. Reports 1998, Vol. 15, pp. 187-204). The tricyclus (IV) is also known in the literature (compounds 16 and 17 in Barrero et al., Eur. J. Org. Chem. 2006, pp. 3434-3441). Caryophyllene oxide (V) is also known in the literature (Siegel et al., Org. Biomol. Chem. 2012, Vol. 10, pp. 383-393).

Step i) of the present process may further comprise the purification of 1-(10,10-dimethyl-7-methylene-4-bicyclo[6.2.0]decanyl)ethanone, in particular 1-[(1R,4R/S,8S)-10,10-dimethyl-7-methylene-4-bicyclo[6.2.0]decanyl]ethanone, obtained from the oxidation reaction as described above, e.g. by distillation.

Preferred distillation devices for the purification of 1-(10,10-dimethyl-7-methylene-4-bicyclo[6.2.0]decanyl)ethanone, in particular 1-[(1R,4R/S,8S)-10,10-dimethyl-7-methylene-4-bicyclo[6.2.0]decanyl]ethanone, are for example distillation columns, such as tray columns optionally equipped with bubble cap trays, sieve plates, sieve trays, packages or filler materials, or spinning band columns, such as thin film evaporators, falling film evaporators, forced circulation evaporators, Sambay evaporators, etc. and combinations thereof. Especially preferred distillation devices for the purification of 1-(10,10-dimethyl-7-methylene-4-bicyclo[6.2.0]decanyl)ethanone, in particular 1-[(1R,4R/S,8S)-10,10-dimethyl-7-methylene-4-bicyclo[6.2.0]decanyl]ethanone, are distillation columns, in particular packed columns, e.g. columns packed with high efficiency structured packing, and spinning band columns.

After distillative purification 1-(10,10-dimethyl-7-methylene-4-bicyclo[6.2.0]decanyl)ethanone, in particular 1-[(1R,4R/S,8S)-10,10-dimethyl-7-methylene-4-bicyclo[6.2.0]decanyl]ethanone, can typically be obtained in high purity, e.g. in a purity of at least 80%. Generally, 1-(10,10-dimethyl-7-methylene-4-bicyclo[6.2.0]decanyl)ethanone is obtained as a non-racemic mixture of the 8 stereoisomers, as defined above. 1-[(1R,4R/S,8S)-10,10-Dimethyl-7-methylene-4-bicyclo[6.2.0]decanyl]ethanone used as the preferred starting material of the hydrogenation reaction in step ii), is usually obtained as a non-racemic mixture of its 4R- and 4S-stereoisomers, as defined above.

Generally, the starting material beta-caryophyllene (CAS-No. 87-44-5) used in step i) of the present process is isolated from clove oil on technical scales and can be readily obtained from commercially sources.

Step ii)

The catalytic hydrogenation of 1-(10,10-dimethyl-7-methylene-4-bicyclo[6.2.0]decanyl)ethanone, in particular 1-[(1R,4R/S,8S)-10,10-dimethyl-7-methylene-4-bicyclo[6.2.0]decanyl]ethanone, corresponding to step ii) of the present process, is carried out using processes and catalysts for the hydrogenation of double bonds that are well known to the person skilled in the art.

Suitable catalysts for the hydrogenation of double bonds are for example catalysts which comprise at least one metal of transition group VIII of the Periodic Table of the Elements, for example platinum, rhodium, palladium, cobalt or ruthenium, preferably ruthenium or palladium, either alone or together with at least one metal from transition group I or VII of the Periodic Table of the Elements, for example copper or rhenium. The transition metal is typically deposited on a support material. Generally, any support material that is described in the state of the art for such catalysts can be used. Suitable support materials are by way of example single or mixed metal oxides, such as zirconium dioxide ($ZrO_2$), zinc oxide (ZnO), magnesium oxide (MgO), titanium dioxide ($TiO_2$), aluminium oxide, $TiO_2$—$Al_2O_3$ or $ZrO_2$—$Al_2O_3$, zeolites (aluminosilicates), hydrotalcite, silicium carbide (SiC), tungsten carbide (WC), silicium dioxide ($SiO_2$), charcoal, activated charcoal, carbon, sulfated carbon, diatomite, clay, barium sulfate, or else a combination thereof.

Other suitable catalysts are likewise nickel-based catalysts, such as Raney catalysts, preferably Raney nickel.

Preferred hydrogenation catalysts that are used in step ii) of the present process are selected from supported Pd-catalysts. A particularly preferred hydrogenation catalysts that is used in step ii) of the present process is Pd on charcoal.

Typically, the metal content of the supported hydrogenation catalyst is in the range of from 0.1 to 30% by weight, preferably in the range of from 0.5 to 20% by weight and in particular of from 1 to 15% by weight.

Typically, the hydrogenation catalyst is applied in an amount of from 0.1 to 25% by weight, preferably in an amount of from 0.5 to 15% by weight, based on the amount of 1-(10,10-dimethyl-7-methylene-4-bicyclo[6.2.0]decanyl)ethanone, in particular 1-[(1R,4R/S,8S)-10,10-dimethyl-7-methylene-4-bicyclo[6.2.0]decanyl]ethanone, in the reaction mixture.

The hydrogenation can take place by analogy to known hydrogenation processes for hydrogenating organic compounds which have hydrogenatable groups. To this end, the organic compound in the form of liquid phase or gas phase, preferably in the form of liquid phase, is brought into contact with the catalyst in the presence of hydrogen. The liquid phase can by way of example be passed over a fluidized bed of catalyst (fluidized bed method) or can be passed over a fixed bed of catalyst (fixed bed method).

In the process of the invention, it is preferable that the hydrogenation takes place in a fixed-bed reactor.

The hydrogenation is generally carried out at a hydrogen pressure in the range from 0.1 to 150 bar, preferably in the range from 0.5 to 100 bar, particularly in the range from 0.8 to 50 bar.

Preferably, the hydrogenation is carried out in the presence of an organic solvent, which is inert under the hydrogenation conditions. Suitable solvents that can be used in the hydrogenation reaction are, for example, aliphatic hydrocarbons, such as pentane, hexane, heptane, ligroin, petrol ether or cyclohexane, aromatic hydrocarbons, such as benzene, toluene or xylenes, esters, such as ethyl acetate, ethers such as methyl-tert.-butylether, dibutyl ether, tetrahydrofuran, 1,4-dioxane or 1,2-dimethoxyethane, lower alkanols, such as methanol, ethanol, isopropanol or tert.-butanol, dialkylene glycol, or mono- or diethers thereof, for example, as well as mixtures of the aforementioned organic solvents.

The hydrogenation is usually carried out at a temperature in the range from 5 to 150° C., particularly preferably of from 10 to 100° C.

The amount of hydrogen used for the hydrogenation is generally from 1 to 15 times the stoichiometric amount of hydrogen theoretically needed for the complete hydrogenation of the double bond of 1-(10,10-dimethyl-7-methylene-4-bicyclo[6.2.0]decanyl)ethanone, in particular 1-[(1R,4lR/S,8S)-10,10-dimethyl-7-methylene-4-bicyclo[6.2.0]decanyl]ethanone.

It is preferred that the catalytic hydrogenation of 1-(10,10-dimethyl-7-methylene-4-bicyclo[6.2.0]decanyl)ethanone, in particular 1-[(1R,4R/S,8S)-10,10-dimethyl-7-methylene-4-bicyclo[6.2.0]decanyl]ethanone, provided in step i) of the present process is carried out under neutral conditions. The term "neutral conditions", as used herein, means that no significant amounts of acid or alkali, in particular acid, are added to the reaction mixture. Likewise, the term "neutral conditions" also means that no acidic or basic materials are used as support material for the hydrogenation catalysts.

In one preferred embodiment of step ii) of the present process, the hydrogenation is carried out in the presence of a supported Pd-catalyst having a Pd content of 1 to 15% by weight and an inert solvent, under a hydrogen atmosphere at a pressure of from 0.8 to 50 bar and at a temperature of from 10 to 100° C., where the supported Pd-catalyst is used in an amount of from 0.1 to 25% by weight, based on the amount of the applied 1-(10,10-dimethyl-7-methylene-4-bicyclo[6.2.0]decanyl)ethanone, in particular 1-[(1R,4R/S,8S)-10,10-dimethyl-7-methylene-4-bicyclo[6.2.0]decanyl]ethanone.

The hydrogenation can be designed to take place either continuously or else batchwise, preference being given here to the continuous design of the process. The batchwise hydrogenation can use a reaction apparatus conventionally used for this purpose, e.g. a stirred reactor. It is preferable that the hydrogenation of the invention is carried out continuously in fixed-bed reactors in upflow mode or downflow mode. The hydrogen here can be passed over the catalyst cocurrently with the solution of the starting material to be hydrogenated, or else in countercurrent, Suitable apparatuses for conducting fluidized-bed-catalyst hydrogenation and fixed-bed-catalyst hydrogenation are known in the prior art, e.g. from Ullmanns Enzyklopädie der Technischen Chemie [Ullmann's Encyclopedia of Industrial Chemistry], 4$^{th}$ edition, volume 13, pp. 135 ff., and also from P. N. Rylander, "Hydrogenation and Dehydrogenation" in Ullmann's Encyclopedia of Industrial Chemistry, 5th edn. on CD-ROM.

In a preferred embodiment of the present process step i) or both steps i) and ii) are performed in a continuous manner. In particular, both steps i) and ii) are performed in a continuous manner.

The process of the present invention may further comprise the purification of the 1-(7,10,10-trimethyl-4-bicyclo[6.2.0]decanyl)ethanone, in particular 1-[(1R,4R/S,7R/S,8S)-7,10,10-trimethyl-4-bicyclo[6.2.0]decanyl]ethanone, obtained in step ii), e.g. by distillation.

Preferred distillation devices for the purification of 1-(7,10,10-trimethyl-4-bicyclo[6.2.0]decanyl]ethanone, in particular 1-[(1R,4R/S,7R/S,8S)-7,10,10-trimethyl-4-bicyclo[6.2.0]decanyl]ethanone, are as described above for the distillative purification of 1-(10,10-dimethyl-7-methylene-4-bicyclo[6.2.0]decanyl)ethanone.

After distillative purification 1-(7,10,10-trimethyl-4-bicyclo[6.2.0]decanyl]ethanone, in particular 1-[(1R,4R/S,7R/S,8S)-7,10,10-trimethyl-4-bicyclo[6.2.0]decanyl]ethanone, can typically be obtained in high purity, e.g. in a purity of at least 80%. Generally, 1-(7,10,10-trimethyl-4-bicyclo[6.2.0]decanyl]ethanone is obtained as a non-racemic mixture of the 16 stereoisomers, as defined above. 1-[(1R,4R/S,7R/S,8S)-7,10,10-trimethyl-4-bicyclo[6.2.0]decanyl]ethanone is usually obtained as a non-racemic mixture of its (4R/S,7R/S)-stereoisomers, as defined above.

EXAMPLES

I) Gas Chromatographic Analysis:
GC-System and Separation Method:
GC-system: Agilent 7890A
GC-Column: HP-5 (60 m (Length), 0.32 mm (ID), 1.0 μm (Film))
Temperature program: 100° C. to 225° C. in 5° C./min, 10 minutes at 225° C., 225° C. to until 280° C. in 5° C./min.

II) Production Examples

Example II.1

Oxidation of Beta-Caryophyllene in Toluene at 230° C. with $N_2O$ (40 Bar)

A 300 mL autoclave is charged with 30.0 g beta-caryophyllene (88 wt.-% obtained from Aldrich Chemicals) in 70.0 g toluene and flushed 3 times with $N_2$ (50 bar). The vessel is then pressurized with $N_2O$ (40 bar) at room temperature. The magnetic stirring is turned on and the autoclave heated to the reaction temperature (230° C.) for 3 hours. During reaction the pressure in the autoclave was about 70-75 bar. After cooling to room temperature and slow depressurization, the solution was analyzed with quantitative GC using dioxane as the internal standard (HP-5 column: 60 m (Length), 0.32 mm (ID), 1.0 μm (Film)/100° C. to 225° C. in 5° C./min, 10 minutes at 225° C., 225° C. to until 280° C. in 5° C./min.). The conversion of beta-caryophyllene was 97%. The yields of (I.b), (II), (III), (IV) and (V) where found to be 40%, 10%, 3%, 1% and 2% respectively.

Example II.2

Oxidation of β-Caryophyllene at 210° C. with $N_2O$ (40 Bar) without Added Solvent A 300 mL autoclave is charged with 100 g beta-caryophyllene (88 wt.-% obtained from Aldrich Chemicals)

and flushed 3 times with $N_2$ (50 bar). The vessel is then pressurized with $N_2O$ (40 bar) at room temperature. The magnetic stirring is turned on and the autoclave heated to the reaction temperature (210° C.) for 3 hours. During reaction the pressure in the autoclave was about 70 to 75 bar. After cooling to room temperature and slow depressurization, the solution was analyzed with quantitative GC using dioxane as the internal standard (HP-5 column: 60 m (Length), 0.32 mm (ID), 1.0 μm (Film)/100° C. to 225° C. in 5° C./min, 10 minutes at 225° C., 225° C. to until 280° C. in 5° C./min.). The conversion of beta-caryophyllene was 58% and the selectivity of (I.b), (II), (III) and (IV) where found to be 59%, 15%, 8% and 2% respectively.

Example II.3

Purification of 1-[(1R,4R/S,8S)-10,10-dimethyl-7-methylene-4-bicyclo[6.2.0]decanyl]ethanone by Distillation The crude product obtained in example II.2 was purified by means of fractional distillation using a spinning band column whereupon 1-[(1R,4R/S,8S)-10,10-dimethyl-7-methylene-4-bicyclo[6.2.0]decanyl]ethanone was obtained in a purity of 99.6%. The identity and purity of the final product was determined by means of GC (Area-% of the FID detector signal). 1-[(1R,4R/S,8S)-10,10-dimethyl-7-methylene-4-bicyclo[6.2.0]decanyl]ethanone consists of a mixture of two diastereoisomers.

Example II.4

Catalytic Hydrogenation of 1-[(1R,4R/S,8S)-10,10-dimethyl-7-methylene-4-bicyclo[6.2.0]decanyl]ethanone 5 g 1-[(1R,4R/S,8S)-10,10-dimethyl-7-methylene-4-bicyclo[6.2.0]decanyl]ethanone obtained in Example II.3, which consists of a mixture of two diastereomers in a ratio of 2:1, was dissolved in 50 mL of Methanol, then 0.5 g of Pd-catalyst (5% on charcoal) was added. The mixture was shaken at room temperature with $H_2$ at barometric pressure. After 6.5 hours, the reaction was stopped. The catalyst was then filtered off over silica gel and washed twice with MeOH. The filtrate was dried over sodium sulfated and the solvent was removed. 4 g 1-[(1R,4R/S,7R/S,8S)-7,10,10-trimethyl-4-bicyclo[6.2.0]decanyl]ethanone were obtained, which corresponds to a yield of 80%.

Example II.5

Purification of 1-[(1R,4R/S,7R/S,8S)-7,10,10-trimethyl-4-bicyclo[6.2.0]decanyl]ethanone by Distillation The crude product obtained in example 11.4 was purified by means of fractional distillation whereupon 1-[(1R,4R/S,7R/S,8S)-7,10,10-trimethyl-4-bicyclo[6.2.0]decanyl]ethanone was obtained in a purity of 97%. The identity and purity of the final product was determined by means of GC (Area-% of the FID detector signal). 1-[(1R,4R/S,7R/S,8S)-7,10,10-trimethyl-4-bicyclo[6.2.0]decanyl]ethanone consists of a mixture of four stereoisomers in a ratio of 8:4:4:1 (determined by $^{13}$C-NMR).

III) Analytical Characterization of 1-[(1R,4R/S,7R/S,8S)-7,10,10-trimethyl-4-bicyclo[6.2.0]decanyl]ethanone The identity of 1-[(1R,4R/S,7R/S,8S)-7,10,10-trimethyl-4-bicyclo[6.2.0]decanyl]ethanone was determined using $^1$H- and $^{13}$C-1D/2D-NMR.

$^{13}$C-NMR-Analysis of the Major Stereoisomer:

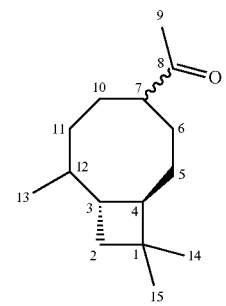

| Atom number | $^{13}$C shifts measured (multiplicity)[1] | $^{13}$C shifts calculated (multiplicity)[2] |
|---|---|---|
| 13 | 16.00 (q) | 18.8 ± 2.0 (q) |
| 14 | 22.52 (q) | 26.0 ± 2.0 (q) |
| 10 | 23.22 (t) | 29.4 ± 2.4 (t) |
| 5 | 24.69 (t) | 25.5 ± 2.4 (t) |
| 6 | 25.29 (t) | 30.9 ± 2.4 (t) |
| 9 | 28.42 (q) | 27.1 ± 2.0 (q) |
| 15 | 30.04 (q) | 26.0 ± 2.0 (q) |
| 11 | 30.32 (t) | 32.8 ± 2.4 (t) |
| 12 | 30.97 (d) | 34.7 ± 3.2 (d) |
| 1 | 33.85 (s) | 34.3 ± 2.8 (s) |
| 2 | 35.01 (t) | 37.7 ± 2.4 (t) |
| 3 | 38.03 (d) | 41.3 ± 3.2 (d) |
| 4 | 43.44 (d) | 48.5 ± 3.2 (d) |
| 7 | 51.44 (d) | 56.5 ± 3.2 (d) |
| 8 | 212.22 (s) | 213.0 ± 3.4 (s) |

[1]The given chemical shifts correspond to the major isomer. The connectivity was unambiguously established with the INADEQUATE pulse sequence.
[2]Calculated with the HOSE-Code Methode (Anal. Chim. Acta. 1978, Vol. 103, pp. 355-365).

IV) Scent Strip Tests

To evaluate the quality and intensity of the odor of 1-[(1R,4R/S,7R/S,8S)-7,10,10-trimethyl-4-bicyclo[6.2.0]decanyl]ethanone, scent strip tests were performed.

For this purpose strips of absorbent paper were dipped into solution containing 1 to 10 wt.-% 1-[(1R,4R/S,7R/S,8S)-7,10,10-trimethyl-4-bicyclo[6.2.0]decanyl]ethanone in ethanol. After evaporation of the solvent (about 30 sec.) the scent impression was olfactorically evaluated by a trained perfumer.

Scent Strip Test Results:
Odor Impression:
Intensity: 2,5; woody: 5; amber: 4; musks: 3; sweet: 3; female: 3
Volatility
long lasting on blotter (>48 h)

As can be deduced from the scent strip test results, 1-[(1R,4R/S,7R/S,8S)-7,10,10-trimethyl-4-bicyclo[6.2.0]decanyl]ethanone is a olfactively valuable compound. The 1-[(1R,4R/S,7R/S,8S)-7,10,10-trimethyl-4-bicyclo[6.2.0]decanyl]ethanone used in these tests was present as a stereoisomer mixture of four stereoisomers, in which 1-[(1R,4S,7R/S,8S)-7,10,10-trimethyl-4-bicyclo[6.2.0]decanyl]

ethanone was found to exhibit the most intensive and characteristic odor impression.

The invention claimed is:

1. 1-(7,10,10-trimethyl-4-bicyclo[6.2.0]decanyl)ethanone.

2. 1-(7,10,10-trimethyl-4-bicyclo[6.2.0]decanyl)ethanone as claimed in claim 1 in the form of 1-[(1R,4R/S,7R/S,8S)-7,10,10-trimethyl-4-bicyclo[6.2.0]decanyl]ethanone.

3. 1-[(1R,4R/S,7R/S,8S)-7,10,10-trimethyl-4-bicyclo[6.2.0]decanyl]ethanone as claimed in claim 2 in the form of a mixture of stereoisomers thereof, which predominantly contains the (4R,7R)- and (4R,7S)-isomer.

4. 1-[(1R,4R/S,7R/S,8S)-7,10,10-trimethyl-4-bicyclo[6.2.0]decanyl]ethanone as claimed in claim 2 in the form of a mixture of stereoisomers thereof, which predominantly contains the (4S,7R)- and (4S,7S)-isomer.

5. 1-[(1R,4R/S,7R/S,8S)-7,10,10-trimethyl-4-bicyclo[6.2.0]decanyl]ethanone as claimed in claim 2 in the form of a mixture of stereoisomers thereof, which predominantly contains the (4R,7R)-isomer, the (4R,7S)-isomer, the (4S,7R)-isomer or the (4S,7S)-isomer.

6. 1-(7,10,10-trimethyl-4-bicyclo[6.2.0]decanyl)ethanone as claimed in claim 1 having a purity of at least 80%.

7. A fragrance or flavor comprising the 1-(7,10,10-trimethyl-4-bicyclo[6.2.0]decanyl)ethanone according to claim 1.

8. The fragrance or flavor of claim 7, where 1-(7,10,10-trimethyl-4-bicyclo[6.2.0]decanyl)ethanone is present in the form of a mixture of stereoisomers thereof, which predominantly contains the (4S,7R)- and (4S,7S)-isomer.

9. The fragrance or flavor of claim 7, wherein the fragrance or flavor is a composition which further comprises a carrier.

10. The fragrance or flavor of claim 9, where the composition is selected from the group consisting of laundry detergents, fabric detergents, cosmetic preparations, fragranced hygiene articles, foods, food supplements, fragrance dispensers, perfumes, pharmaceutical preparations and crop protection compositions.

11. A method of imparting or modifying a scent or a flavor to a composition, which method comprises incorporating the 1-(7,10,10-trimethyl-4-bicyclo[6.2.0]decanyl)ethanone according to claim 1 into a composition in such an amount that imparts or modifies the scent or flavor of the composition.

12. A fragrance containing composition and/or a fragrance material, which comprises the 1-(7,10,10-trimethyl-4-bicyclo[6.2.0]decanyl)ethanone according to claim 1 and a carrier material.

13. A process for preparing 1-(7,10,10-trimethyl-4-bicyclo[6.2.0]decanyl)ethanone, which comprises
i) providing 1-(10,10-dimethyl-7-methylene-4-bicyclo[6.2.0]decanyl)ethanone,
ii) hydrogenating 1-(10,10-dimethyl-7-methylene-4-bicyclo[6.2.0]decanyl)ethanone with hydrogen in the presence of a hydrogenation catalyst.

14. The process of claim 13, where the composition containing 1-(10,10-dimethyl-7-methylene-4-bicyclo[6.2.0]decanyl)ethanone provided in step i) is obtained by reacting 4,11,11-trimethyl-8-methylene-bicyclo[7.2.0]undec-4-ene with $N_2O$.

15. The process of claim 14, where (4R,4E,9S)-4,11,11-trimethyl-8-methylene-bicyclo[7.2.0]undec-4-ene is reacted with $N_2O$ to obtain 1-[(1R,4R/S,8S)-10,10-dimethyl-7-methylene-4-bicyclo[6.2.0]decanyl]ethanone.

16. The process of claim 13, where step i) or both steps i) and ii) are performed in a continuous manner.

17. The process of claim 13, further comprising the purification of the reaction mixture obtained in step ii) by distillation.

* * * * *